United States Patent [19]
Williams et al.

[11] Patent Number: 5,194,373
[45] Date of Patent: Mar. 16, 1993

[54] METHOD OF DETERMINING ENDOTHELIAL CELL COVERAGE OF A PROSTHETIC SURFACE

[75] Inventors: Stuart K. Williams, Wilmington, Del.; Bruce E. Jarrell, Philadelphia, Pa.

[73] Assignee: Thomas Jefferson University, Philadelphia, Pa.

[21] Appl. No.: 615,985

[22] Filed: Nov. 20, 1990

Related U.S. Application Data

[63] Continuation-in-part of Ser. No. 927,745, Nov. 6, 1986, abandoned, which is a continuation-in-part of Ser. No. 848,453, Apr. 4, 1986, abandoned, which is a continuation-in-part of Ser. No. 742,086, Jun. 6, 1985, Pat. No. 4,820,626.

[51] Int. Cl.$^5$ .......................... C12Q 1/06; C12Q 1/04; C12N 5/00; C12N 5/08
[52] U.S. Cl. .................................. 435/34; 435/240.2; 435/240.23; 435/240.241; 435/39
[58] Field of Search ...................... 435/29, 240.241, 39, 435/34, 240.2, 240.23

[56] References Cited

U.S. PATENT DOCUMENTS 4,820,626  4/1989  Williams et al. ..................... 435/1

OTHER PUBLICATIONS

Graham et al. Expanded Polytetrafluoroethylene Vascular Prosthesis Seeded With Enzymatically Derived and Cultured Canine Endothelial Cells. Surgery, vol. 91, No. 5, pp. 550–559, 1982.
Herring et al., Seeding Arterial Prostheses with Vascular Endothelium The Nature of the Lining. Annals of Surgery, vol. 190, No. 1, pp. 84–90, 1979.
Summerhayes, et al. Unusual Retention of Rhodamine 123 by Mitochondria in Muscle and Carcinoma Cells. Proc. Natl. Acad Sci. USA, vol. 79, pp. 5292–5296, 1982.
Chen et al., Probing Mitochondaria in Living Cells with Rhodamine 123: Cold Spring Harbor Symposium on Quantitative Biology, vol. 46, pp. 141–154, 1982.

Nature "New On The Market" Nature, vol. 343, p. 97, Jan. 4, 1990.

(List continued on next page.)

Primary Examiner—David L. Lacey
Assistant Examiner—George C. Elliott
Attorney, Agent, or Firm—Woodcock Washburn Kurtz Mackiewicz & Norris

[57] ABSTRACT

Determination of effectiveness of microvascular endothelial cell seeding upon a vascular graft surface within the operating room environment would be desirable to maintain quality control in any clinical trial. A number of fluorescent dyes including mithramycin, Hoechst 33342, sulfofluorescein diacetate, Nile Red, rhodamine 123, and PKH26-GL were evaluated for their ability to fluorescently label uncultured microvascular endothelial cells on graft material and subsequently allow determination of seeded cell number and cell spreading. Rhodamine 123 and PKH26-GL produced the most desirable characteristics. The selected non-toxic fluorescent dyes allowed excellent cell visualization after a 30 minute incubation. Unlike the other fluorescent dyes evaluated, the selected non-toxic fluorescent dyes caused the cellular cytoplasm to fluoresce bright orange at a 510 nm excitation wavelength while the underlying polyethyleneterephthalate polyester or expanded polytetrafluorethylene demonstrated minimal autofluorescence. No inhibitory effect on cell attachment to plastic or subsequent cell growth in culture was observed. This technique is useful in the operating room to visualize part or all of an microvascular endothelial cell-seeded graft and to permit a quantitative as well as qualitative evaluation of the seeding process to enhance graft patency.

14 Claims, 6 Drawing Sheets

OTHER PUBLICATIONS

Edwards, W. H. and Mulherin, J. L. The Role of Graft Material in Femorotibial Bypass Grafts *Ann. Surg.* 191:721, 1980.

Herring, M. et al., Seeding Human Arterial Prosthesis with Mechanically Derived Endothelium. *J. Vasc. Surg.*, 1984, 1 (2), 279–289.

Williams, S. et al., Adult Human Endothelial Cell Compatibility with Prosthetic Graft Material *J. Surg. Res.* 38:618, 1985.)

Baker, K. S. et al. Endothelialization of Human Collagen Surfaces with Human Adult Endothelial Cells. *Amer. J. Surg.* 150:197, 1985.

Durand, R., and Olive, P. Cytotoxicity, Mutagenicity and DNA Damage by Hoechst 33342 *J. Histochem. Cytochem.* 30:111, 1982.

Williams, S. et al., Quantitative Determination of Deoxyribonucleic Acid from Cells Collected on Filters. *Anal. Biochem.* 107:17, 1980.

Greenspan, P. et al., Nile Red: A Selective Fluorescent Stain for Intracellular Lipid Deposits. *J. Cell. Biol.* 100:965, 1985.

Johnson, L. et al., Localization of Mitochondria in Living Cells with Rhodamine 123. *P.N.A.S.. U.S.A.* 77:990, 1980.

Jarrell, B. et al., Human Adult Endothelial Cell Growth in Culture. *J. Vasc. Surg.* 6:757, 1984.

Thornton, S. et al., Human Endothelial Cells: Cloning and Long-term Serial Cultivation Employing Heparin. *Science* 222:623, 1983.

Jaffe, E. A. et al., C. Culture of Human Endothelial Cells Derived from Umbilical Veins. *J. Clin. Invest* 52:2745, 1973.

Arndt-Jovin, D., and Jovin, T. Analysis and Sorting of Living Cells According to Deoxyribonucleic Acid Content. *J. Histochem. Cytochem.* 25:585, 1977.

Johnson, L. et al., Decreased Uptake and Retention of Rhodamine 123 by Mitochondria in a Feline Sarcoma Virus-transformed Mink Cells. *Cell*, 28:7, 1982.

Chen. L. et al., Probing Metochondria in Living Cells with Rhodamine 123. *Cold Spring Harbor Symposium Quant. Biol.* 46:141, 1982.

Ziegler, M. and Davidson, R. Elimination of Mitochondrial Elements and Improved Viability in Hybrid Cells. *Somatic Cell Genetics,* 7:73, 1981.

Herring et al. *Biol. Abstr.* 69(3):1559 (1979).

METHOD OF DETERMINING ENDOTHELIAL CELL COVERAGE OF A PROSTHETIC SURFACE

CROSS-REFERENCE TO RELATED APPLICATIONS

The present application is a continuation-in-part of our prior copending U.S. Pat. application Ser. No. 927,745, now abandoned, filed Nov. 6, 1986 entitled "Method of Determining Endothelial Cell Coverage of a Prosthetic Surface", which is a continuation-in-part of application Ser. No. 848,453 filed Apr. 4, 1986, now abandoned, entitled "A Method of Treating A Synthetic or Naturally Occurring Surface with a Collagen Laminate to Support Microvascular Endothelial Cell Growth and the Surface Itself", which in turn is a continuation-in-part of our prior U.S. Pat. application Ser. No. 742,086, filed Jun. 6, 1985 entitled "A Method of Treating a Synthetic or Naturally Occurring Surface With Microvascular Endothelial Cells and the Treated Surface Itself", which has now issued as U.S. Pat. No. 4,820,626, each of which applications is assigned to the assignee of the present application, which applications are hereby incorporated by reference.

This application is also related to copending application Ser. No. 210,218 filed Jun. 17, 1988, now issued U.S. Pat. No. 4,994,387 which is a continuation application of Ser. No. 550,305, filed Nov. 10, 1983, now abandoned, in the names of Elliott Levine, Sandor S. Shapiro and Bruce Jarrell, entitled "Process And Medium for Cloning and Long Term Serial Cultivation of Human Endothelial Cells", and its continuation application Ser. No. 848,913, filed Apr. 7, 1986, now abandoned, portions of which are owned by the assignee hereof, which application is also incorporated by reference as if fully set forth herein.

BACKGROUND OF THE INVENTION

In the specification, footnotes used are to the following references, which are hereby incorporated by reference into the specification.

1. Edwards, W. H. and Mulherin, J. L. The role of graft material in femorotibial bypass grafts *Ann. Surg.* 191:721, 1980.
2. Herring, M., Gardner, A., Glover, J., Seeding human arterial prosthesis with mechanically derived endothelium. The detrimental effect of smoking, *J. Vasc. Surg.*, 1984, 1 (2), 279-289.
3. Williams, S., Jarrell, B., Friend, L., Radomski, J., Carabasi, R., Koolpe, E., Mueller, S., Thornton, S., Marinucci, T., and Levine, E. Adult human endothelial cell compatibility with prosthetic graft material. *J. Surg. Res.* 38:618, 1985.
4. Jarrell, B., Williams, S., Solomon, L., Speicher, L., Koolpe, E., Radomski, J., Carabasi, R., Greener, D., and Rosato, F. Use of an endothelial monolayer upon a vascular graft prior to implantation: temporal dynamics and compatibility with the operating room. *Ann. Surg*, Vol. 203 No. 6, 671-678, 1986.
5. Jarrell, B., Williams, S., Stokes, G., Hubbard, F., Carabasi, R., Koolpe, E., Greener, D., Pratt, K., Radomski, J., Speicher, L., and Moritz, M. Use of freshly isolated capillary endothelial cells for the immediate establishment of a monolayer on a vascular graft at surgery. *Surgery* Vol. 100, No. 2, 392-399, 1986.
6. Radomski, J., Jarrell, B., Williams, S., Koolpe, E., Greener, D., and Carabasi, R. Initial adherence of human capillary endothelial cells to Dacron, *J. Surg. Res.* Vol. 42, 133-140, 1987.
7. Baker, K.S., Williams, S., Jarrell, B., Koolpe, E., and Levine, E. Endothelialization of human collagen surfaces with human adult endothelial cells. *Amer. J. Surg.* 150:197, 1985.
8. Durand, R., and Olive, P. Cytotoxicity, mutagenicity and DNA damage by Hoechst 33342 *J. Histocgem Cytochem.* 30:111, 1982.
9. Williams, S., Sasaki, A., Matthews, M., and Wagner, R. Quantitative determination of deoxyribonucleic acid from cells collected on filters. *Anal Biochem.* 107:17, 1980.
10. Greenspan, P., Mayer, E., and Fowler, S., Nile Red: a selective fluorescent stain for intracellular lipid deposits. *J. Cell. Biol.* 100:965, 1985.
11. Johnson, L., Walsh. M., and Chen, L. Localization of mitochondria in living cells with rhodamine 123. *P.N.A.S.. U.S.A.* 77:990, 1980.
12. Jarrell, B., Shapiro, S., Williams, S., Carabasi, R., Levine, E., Mueller, S., and Thornton, S. Human adult endothelial cell growth in culture. *J. Vasc. Surg.* 6:757, 1984.
13. Thornton, S., Mueller, S., and Levine, E. Human endothelial cells: cloning and long-term serial cultivation employing heparin. *Science* 222:623, 1983.
14. Jaffe, E. A., Nachman, R., Becker, C., and Minick, C. Culture of human endothelial cells derived from umbilical veins. *J. Clin. Invest* 52:2745, 1973.
15. Arndt-Jovin, D., and Jovin, T. Analysis and sorting of living cells according to deoxyribonucleic acid content. *J. Histochem. Cytochem* 25:585, 1977.
16. Johnson, L., Summerhayes, I., and Chen, L. Decreased uptake and retention of rhodamine 123 by mitochondria in a feline sarcoma virus-transformed Mink cells. *Cell*, 28:7, 1982.
17. Chen, L., Summerhayes, I., Johnson, L., Walsh, M., Bernal, S., Lampidis, T, Probing metochondria in living cells with rhodamine 123. *Cold Spring Harbor Symposium Quant. Biol.* 46:141, 1982.
18. Ziegler, M. and Davidson, R. Elimination of mitochondrial elements and improved viability in hybrid cells. *Somatic Cell Genetics*, 7:73, 1981.

Graham et al. *Surgery* 91(5):550-559 (1982) teach harvesting large vessel endothelial cells from dog external jugular veins, culturing the harvested cells, and implanting the seeded grafts in dogs for several weeks. The grafts are then removed and graft segments prepared for study by SEM, TEM and light microscopy. Representative 1.0 sq. cm specimens of the grafts are prepared for $AgNO_3$ staining by rinsing in a 5% glucose solution for 5 minutes, then placing them in a 0.5% $AgNO_3$ solution in direct sunlight until discoloration becomes apparent, rinsing and then fixing in formalin for microscopic examination. Graham et al. also teach fixing graft segments in glutaraldehyde, dehydrating in ethanol, and embedding or critical-point drying for scanning electron microscope (SEM) observation. For light microscopy Graham et al. teach staining with methylene blue. For transmission electron microscopy (TEM), Graham et al. teach fixing in glutaraldehyde and embedding in Epon. From these animal studies, Graham et al. seek to test the efficacy of endothelial cell seeding on excised ePTFE grafts.

Herring et al. *Biol Abstr.* 69(3):1559 (1979) teaches seeding a graft with endothelial cells, implanting the grafts in dogs and then removing the grafts 6 weeks later for examination. F VIII-RA is used to stain the cells lining the excised graft. Silver nitrate Hautchen and EM preparations show a lining pattern characteristic of vascular endothelium.

Summerhayes et al. *Proc. Natl. Acad. Sci. USA* 79:5292-5296 (1982) teach Rhodamine 123 as a mitochondria-specific fluorescent probe in living cells, particularly useful for studying cancer cells for either diagnostic or chemotherapeutic monitoring purposes. In Table 1, on page 5294, Summerhayes et al. show Rhodamine retention of various normal cell types, including human aorta and bovine aorta endothelial cells. This data shows the unusual retention of Rhodomine 123 by mitochondria in muscle or carcinoma cells.

Williams et al. *Anal. Biochem.* 107:17-20 (1980) teach a modified fluorescence assay for the quantitation of cellular DNA extracted from mammalian cells collected on cellulose triacetate membrane filters using mithramycin.

Chen et al. *Cold Spring Harbor Symposia Quant. Biol.* 46:141-155 (1985) teach using Rhodamine 123 for visualizing mitochondria in live cells and as a measure of cell viability after cytotoxic drug exposure. According to Chen et al.'s methods cell aliquots are stained and then analyzed by flow cytometry. Some mitochondria prepared according to Chen et al.'s methods can also be observed with phase-contrast optics.

Greenspan et al. *J. Cell Biol.* Abstract No. 9629, 100(3) 965-974 (1985) teach using Nile red as a fluorescent lipid stain for fluorescence microscopy and flow cytometry.

None of these references teach or suggest using a non-toxic fluorescent dye to evaluate the extent of microvascular endothelial cell coverage or the extent of cell-to-cell interactions on a prosthetic surface prior to implantation.

The replacement of damaged blood vessels with prosthetic vascular grafts has become a feasible surgical option in recent years. While the use of large lumen grafts has met with considerable success, small lumen grafts often become occluded due to the thrombogenic nature of the materials. Attempts have been made to reduce the thrombogenicity of the grafts by seeding with endothelial cells prior to implantation. While this method has proved feasible in animal models, similar attempts using human endothelial cells have not demonstrated improved patency (2).

A procedure for attaching human endothelial cells to vascular graft material in vitro has been recently developed (3). It is now possible to establish an endothelial cell monolayer on a graft after a 1 to 2 hour incubation period (4-7). Before this technique can be performed in the operating room, however, a simple method to determine the completeness of the seeding process is necessary. Present methods to visualize endothelial cells on graft material involve fixation procedures which irreversibly damage the cells. Accordingly, there remains a need for a relatively rapid, non-destructive, method of determining the degree of confluence of seeded endothelial cells on a prosthetic surface.

SUMMARY OF THE INVENTION

The present invention provides a method of determining uncultured microvascular endothelial cell coverage on a prosthetic surface, comprising (a) providing a prosthetic surface which is at least translucent to light in a selected wavelength range;

(b) applying uncultured microvascular endothelial cells at greater than 50% confluence to said surface;

(c) staining said microvascular endothelial cells with a dye capable of exhibiting fluorescent emission in said selected wavelength range; and (d) illuminating said microvascular endothelial cells with a light to excite said emission to permit observation of the cell coverage of said prosthetic surface.

The present invention, therefore provides a valuable diagnostic method in which the degree of completeness with which a prosthetic graft has been covered with uncultured microvascular endothelial cells can be determined. After completion of the steps necessary to allow a monolayer of endothelial cells to form, it is very desirable, if not necessary, to know whether a monolayer truly exists before actual implantation of the graft. This quality control step is necessary to avoid implanting a graft that fails to endothelialize and therefore that would be doomed to thrombosis and failure. For example, it is difficult to visualize living endothelial cells on polyester (such as polyethyleneterephthalate polyester) or expanded polytetrafluoroethylene ("ePTFE") surfaces because of their opacity at visible light wave lengths and autofluorescence in the 400 to 500 nm wavelength range. It has been found that cell number can be determined by staining with conventional nuclear dyes, but that this method is destructive and gives little information regarding cell spreading or cell-to-cell contact. According to the present invention, therefore, cell visualization is preferably performed using either cytoplasmic dyes or dyes that exhibit fluorescent emission in the 500 to 600 nm wavelength range. Preferably, dyes having both characteristics are used. It is further preferred that the method of the invention be performed on the actual graft itself rather than on a "control" segment of cell-seeded graft material. Accordingly, the dye should be non-toxic and acceptable for intra-arterial use.

In the study leading to the present invention, alternate fluorescent dyes were used to stain human endothelial cells in vitro. These included the bisbenzamide stain Hoechst 33342, which intercalates between adenine and thymidine base pairs in DNA and has been demonstrated to be non-toxic at low concentrations (8); mithramycin, an anti-tumor antibiotic which intercalates between guanine and cytosine base pairs (9); Nile Red, a lipophilic dye specific for cytoplasmic lipid vesicles (10); sulfoflurorescein diacetate (SFDA), a cytoplasm-specific dye; rhodamine 123, a dye specific to mitochondria (11); and PKH26-GL (Zynaxis Cell Sciences, Inc., Malvern, PA), a fluorescent cell linker compound which works by selective partitioning into the lipid regions of the cell membrane. We have found that of these compounds, rhodamine 123 and PKH26-GL exhibit the most desirable characteristics. Rhodamine 123 emits a bright orange color when excited with 510 nm light. After a brief exposure to this dye, endothelial cells fluoresce orange while the underlying polyethyleneterephthalate polyester, ePTFE, or polyvinyl alcohol surfaces show little dye uptake or autofluorescence. Rhodamine 123 selectively stains cytoplasmic structures, allowing visualization of the cell margins. It has no permanent effect on endothelial cell growth or attachment properties in vitro and is non-toxic. Cells labelled with PKH26-GL were found to grow at the same rate as identical cells that were not treated with the dye.

The simplicity of the technique makes it compatible with use in the operating room. A microvascular endothelial cell seeded graft can be rapidly evaluated for the number of cells present, the degree of cell spreading as well as the quality of the cell-to-cell interaction prior to graft implantation.

BRIEF DESCRIPTION OF THE DRAWINGS

FIG. 6 is representative of the images which were observed.

DETAILED DESCRIPTION OF THE INVENTION

Figure 1:
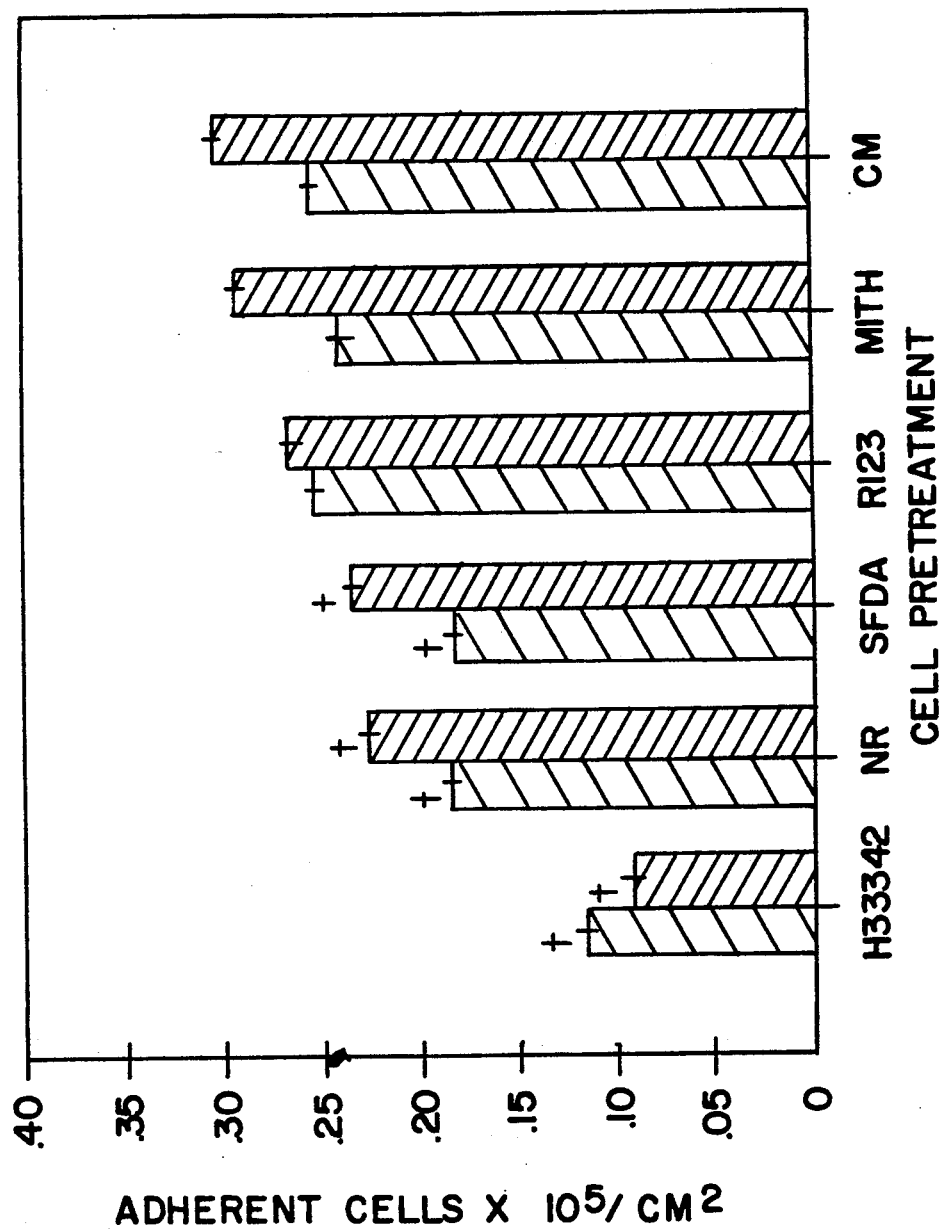
FIG. 1: The effects of H33342, Nile Red (NR), SFDA, Rhodamine 123 (R123), Mithramycin (Mith) and plain culture, medium (CM) on endothelial cell adherence to polystyrene. Human microvessel endothelial cells were incubated for 90 minutes in medium containing 20 $\mu$g/ml H33342, 10 $\mu$g/ml Nile Red, 20 $\mu$g/ml SFDA, 10 $\mu$g/ml rhodamine 123 or 10 $\mu$g/ml mithramycin. After incubation, $1.96 \times 10^4$ cells/cm$^2$ were seeded onto gelatin coated polystyrene. These labelled cells were left in contact with the surface for 60 or 120 minutes and followed by vigorous washing. The number of remaining adherent cells was determined by brief trypsinization and counting with a Coulter Counter. Each adherence study was performed in triplicate. Results were evaluated by calculation of the mean ± the standard error of the mean and compared using the Student's T-test. Statistical significance was present for p less than 0.05 (+). H33342, Nile Red and SFDA demonstrated a statistically significant decrease in cell adherence at both 60 and 120 minutes when compared to unlabelled cells (CM).

The ability to isolate and grow human adult endothelial cells in culture has allowed an in-depth evaluation of endothelial cell functional properties (3). One area of intense investigation has been directed at understanding the variables that affect endothelial cell-prosthetic surface interactions (3). The optimal conditions for cell adherence and proliferation have not yet been determined. Once these conditions are defined, it may be possible to completely coat the lumen of a vascular graft with endothelial cells in the operating room prior to implantation. This theoretically might minimize thrombus formation and early graft failure. One major obstacle to understanding the process of monolayer formation has been the inability to observe endothelial cells directly upon graft material. Prior to the development of the technique described in this specification, most visualization procedures required permanent fixation of samples at multiple experimental time points to evaluate the effects of different conditions. Permanent fixation not only kills cells but also introduces potential artifacts.

Many efforts have been directed at harvesting and culturing endothelial cells. Applicants discovered that the shortcomings of prior art endothelializing methods could be overcome by treating an implant with human microvascular endothelial cells obtained from the tissue of the patient to receive the implant. They recognized that human microvascular endothelial cells will function suitably in place of large vessel cells even though there are morphological and functional differences between large vessel endothelial cells and microvascular endothelial cells in their native tissues. Importantly, microvascular cells are present in an abundant supply in body tissue, most notably fat tissue, and may be used to establish a degree of preimplantation confluence which dramatically improve the prognosis of most implants. By using microvascular endothelial cells, the need to culture adult endothelial cells to increase their numbers prior to implantation is obviated, and the patient is able to receive a graft which has been treated up to or above confluence with his own fresh, "healthy" endothelial cells. Moreover, the cells may be harvested from the patient's fat tissue and the endothelial cell-treated graft may be implanted in a single, uninterrupted surgical procedure. Therefore, it is important to have a rapid and accurate means to assess the extent of endothelial cell coverage. The instant invention provides a method to determine the extent of cell coverage and cell-to-cell interactions quickly and efficiently in the operating room setting.

Neither Graham et al. nor Herring et al. teach a method of evaluating uncultured, microvascular endothelial cell coverage on a graft prior to implantation in a patient. Graham et al. teach harvesting large vessel endothelial cells from dog external jugular veins, culturing the harvested cells for a period of time, and then implanting seeded grafts in dogs for several weeks. The grafts are then removed and graft segments prepared for study by light or electron microscope. Herring et al. teaches seeding of large vessel endothelial cells, implanting the grafts in dogs and then removing the grafts six weeks later for observation. F VIII-RA or silver nitrate is used to stain the cells. These techniques, which kill these large vessel endothelial cells prior to observation, are totally inappropriate for solving the problem of the instant invention.

Figure 6:
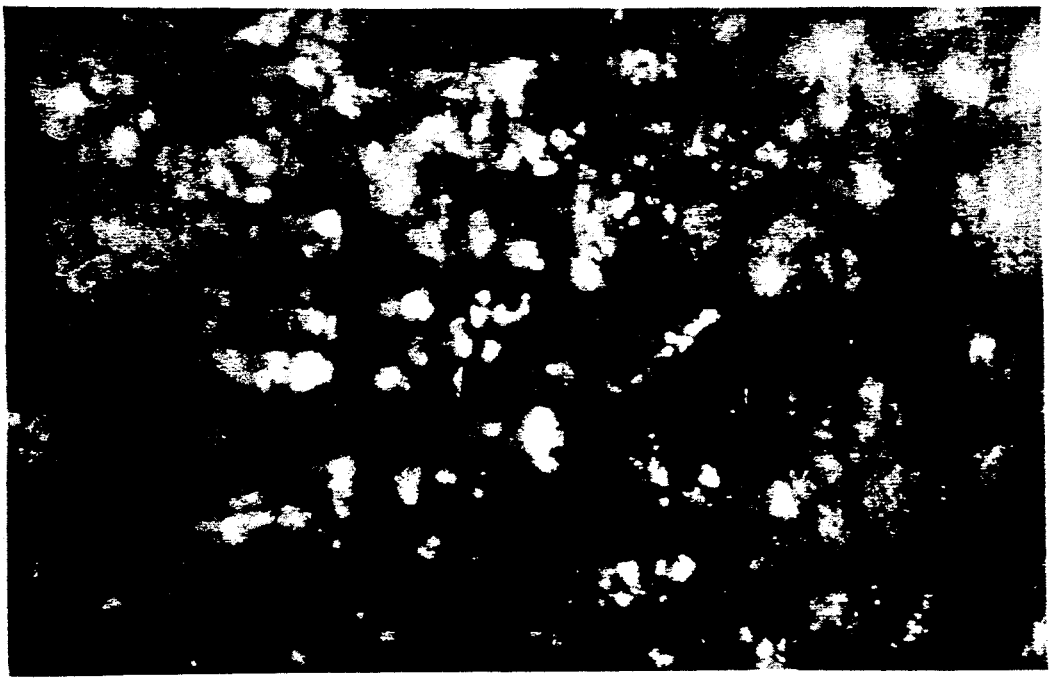
FIG. 6: A fluorescent micrograph representing a surface of a vascular graft which has been treated with fluorescently labelled microvascular endothelial cells and then implanted into a dog's carotid artery for 3 weeks. At the time the graft was explanted from the animal, it was observed by fluorescence microscopy

Further, Graham et al. or Herring et al. do not disclose the seeding of vascular prostheses with uncultured human microvascular endothelial cells. Rather, Graham et al. studied the growth of large vessel endothelial cells which were cultured to obtain enough endothelial cells to seed a graft. Graham et al. recognized one of the problems inherent in the art which the present invention helps abate, i.e., obtaining sufficient quantities of cells for adequate graft coverage. Graham et al.'s large vessel seeding technique requires the cells to undergo numerous duplications which could subsequently reduce the concentration of the dyes in the cells at the time that they were put into the graft. The use of microvessel endothelial cells does not require the cells to undergo numerous duplications, in fact, these cells do not appear to undergo even a single duplication. For example, as shown in FIG. 6, the distribution of fluorescently labelled cells across the surface of the graft was similar from the proximal to the distal end of the graft. The graft was 6 cm in length and was completely covered with fluorescently labelled cells as represented in this Figure. This data shows that (1) the PKH26-GL dye was non-toxic to the cells since they existed for greater than 3 weeks in vivo and (2) that fluorescence is not lost from the cells during their time of implantation. The prior art does not suggest the use of uncultured microvascular endothelial cells or staining or observation methods which would be appropriate for determining the viability and coverage of such cells on a graft surface. The focus of prior art studies was evaluating graft patency after a graft was implanted in a dog for a period of weeks. The dog was killed, the graft excised, and the cells killed prior to observation. This is dramatically different from the purpose and method of the present invention wherein live, uncultured microvascular endothelial cells are harvested from a patient's own fat, seeded onto a graft at extremely high density which is then evaluated in accordance with the teachings of the present invention prior to implantation in the patient. Prior to the development of the technique of the present invention, visualization procedures, such as those described by Graham et al. and Herring et al., required permanent fixation of samples which not only kills cells but also introduces potential artifacts. Therefore the prior art teaches away from the present invention which concerns a rapid, easily performed, non-toxic method for microvascular endothelial cell visualization on graft materials.

Further, the prior art does not teach or suggest using a dye to evaluate the extent of human microvascular endothelial cell coverage or the extent of cell-to-cell interactions on a prosthetic surface prior to implantation. The method of the present invention is performed on the actual graft to be implanted, rather than on a control segment of cultured cell-seed graft. Further, the instant invention does not involve fixing and embedding graft segments for later study, but rather allows almost immediate evaluation of cell coverage and cell-to-cell interactions, prior to implantation of the stained graft.

The purpose of using a vital stain is to prevent damage to the microvascular endothelial cells and to maintain a biocompatible graft. The use of the selected fluorescent dye in the present invention is different from the prior art in that a dye must be selected so that the uncultured fluorescently labelled microvascular endothelial cells can be placed onto the graft at very high density, i.e., greater than 50% confluence. The dye must also be capable of remaining with the cells for extended periods of time once the grafts are implanted. The in vitro growth data shown in FIG. 4 demonstrates that canine microvascular endothelial cells labelled with a fluorescent dye known as PKH26-GL (Zynaxis Cell Science Inc., Malvern, PA) grow at the same rate as identical cells which have not been treated with the fluorescent dye. Therefore, this dye is non-toxic to microvascular endothelial cells. FIG. 5 shows microvascular cells which have been treated with this same fluorescent dye showing the distribution of fluorescence within the individual cells. The dark areas within each cell are the nucleus of the cell which does not take up the fluorescent dye.

The purpose of the study leading to the present invention was the development of a rapid, easily performed non-toxic method for endothelial cell visualization on polyethyleneterephthalate polyester, ePTFE, polyvinyl alcohol, and other graft materials. We examined a group of fluorescent dyes which have numerous applications in cell biology ranging from the visualization of cytoplasmic components (10, 11) to flow cytometry (15). Our results demonstrated that rhodamine 123 and PKH26-GL were the most useful for visualizing uncultured microvascular endothelial cells on woven polyethyleneterephthalate polyester, ePTFE and PVA.

Rhodamine 123 has been used in histology for comparing normal and transformed fibroblasts (16), assessing the efficacy of chemotherapy (17) and selection of cells containing mutations (18). Its specificity for mitochondria appears to be due to the high negative charge within the mitochondria and the strongly positive charge of rhodamine 123 at physiological pH. For our purposes, rhodamine 123 has several desirable features. It is readily assimilated into the cells in a concentration-dependent manner and is relatively non-toxic to the cells. While cytostatic when maintained in culture, brief exposure to the dye followed by culture in non-dye containing medium has little demonstrable detrimental effect. The vehicle, 0.1% DMSO, also has an insignificant effect on cells with respect to adherence or growth. This apparent lack of toxicity permits treatment of microvascular endothelial cells with rhodamine 123 and then seed them onto polyethyleneterephthalate polyester, ePTFE or PVA in plain medium without affecting cell adherence or growth. Finally, rhodamine 123 fluoresces at a wavelength where the autofluorescence of polyethyleneterephthalate polyester, ePTFE and PVA is negligible.

PKH26-GL is a fluorescent cell linked compound which works by selective partitioning into the lipid regions of the cell membrane. As shown in FIG. 6, a fluorescent micrograph representing the surface of a vascular graft which has been treated with fluorescently labelled microvascular endothelial cells and then implanted into a dog's carotid artery for 3 weeks and then explanted and observed by fluorescence microscopy, the distribution of fluorescently labelled cells across the surface of the graft was similar from the proximal to the distal end of the graft. The cells in this micrograph have a high degree of fluorescence qualitatively identical to the fluorescence at the time of graft sodding. This data shows that the dye is non-toxic to the cells since they existed for greater than 3 weeks in vivo and that the fluorescence is not lost from the cells during the time of implantation.

The ability to visualize human endothelial cells on vascular graft material has two major applications. In the laboratory, fluorescent labeling of endothelial cells with a selected fluorescent dye allows direct observation of the morphological response of living cells to various experimental conditions. As a consequence, the variables affecting endothelial cell adherence and growth on vascular grafts can be evaluated in real time rather than following chemical fixation. Once these conditions are defined, it may be possible to refine current graft seeding techniques.

In the clinical setting, this technique is useful for assessing the extent of endothelial cell seeding on vascular grafts in the operating room. We have demonstrated that large numbers of microvascular endothelial cells can be rapidly harvested from small quantities of human fat (5). The number of cells obtained is sufficient to allow graft seeding at confluent densities, i.e., greater than 50% confluence without the need for cell culture. In addition, we have demonstrated that these endothelial cells have the potential to establish a confluent monolayer on certain vascular grafts in less than one hour. One concern with this system is the ability to rapidly assess the completeness of microvascular endothelial cell seeding on a graft prior to implantation. One potential method of performing this quality control step is direct fluorescent visualization of the final monolayer using a selected fluorescent dye. This selected non-toxic fluorescent dye allows rapid visualization of endothelial cells and permits assessment of both the number of cells present and the quality of cell-to-cell interactions.

Methods

Isolation of Human Fat Microvessel Endothelial Cells

Human perirenal and mental fat were obtained from cadaver renal donors. Appropriate institutional review procedure was followed. Microvessel endothelial cells were isolated by mechanical mincing, digestion with collagenase (Worthington Type I; Worthington Diagnostic Systems, Freehold, N.J.) at a concentration of 4 mg/ml, followed by density gradient centrifugation in 45% Percoll (Pharmacia Fine Chemicals, Piscataway, N.J.) (5). The cells were grown in 25 cm$^2$ culture flasks which had been pretreated with a 1% gelatin solution. The culture medium consisted of medium 199 with 20% heat-inactivated fetal calf serum, 90 µg/ml porcine heparin, and 20 µg/ml Endothelial cell Growth Factor (ECGF) (12,13). The cells were incubated at 37° C. in a 5% CO$_2$ atmosphere and at confluence reached a density of 10$^5$ cells per cm$^2$.

Isolation of Large Vessel Endothelial Cells

Human large blood vessels were cleaned of their surrounding fascia and rinsed with culture medium (14). The ends of the vessel were cannulated and the lumen treated with collagenase (Worthington Type I, Worthington Diagnostic Systems, Inc., Freehold, N.J.) to dislodge the endothelial cells from the inner wall. The vessels were then flushed with culture medium to collect the cells. The large vessel cells were cultured under conditions identical to that used for the microvessel endothelial cells.

Preparation of Graft Materials

Graft materials made of woven polyethyleneterephthalate polyester (Meadox Medicals, Inc.) and ePTFE (W.L. Gore, Inc.) were immobilized in plastic rings (Beem capsule, Polysciences, Fort Washington, PA) with a 0.5 cm$^2$ surface area. Polyvinyl alcohol (PVA), a hydrogel not presently used for vascular grafts, was glued to the end of glass tubing of the same dimensions. Prior to use, the polyethyleneterephthalate polyester and ePTFE were degreased by washing sequentially with acetone, 8.5% phosphoric acid, 1 N sodium hydroxide and distilled water. The graft material was then dried thoroughly and gas sterilized. The PVA was hydrated in PBS for at least 24 hours prior to use.

Preparation of Platelet Rich Plasma

Fresh human blood was drawn into tubes containing sodium citrate. The blood was centrifuged for 6 minutes at 300×g. The supernatant was combined with calcium chloride to a final concentration of 20 mM. Two hundred µl of this solution were immediately used to coat the polyethyleneterephthalate polyester and ePTFE at the bottom of each Beem capsule and forced through the graft by means of a micropipette. When clotting was completed residual clot was removed from the graft by aspiration. PVA underwent no pretreatment other than hydration.

Seeding of Endothelial Cells

Confluent flasks of endothelial cells were treated for several minutes with a solution containing 0.25% trypsin and 0.04% EDTA in buffered Hank's salts. When the cells had lifted from the bottom of the flask, culture medium was added to inactivate the trypsin. Cells were seeded onto the graft at densities up to 10$^5$ cells per cm$^2$.

Light Microscopy

Seeded grafts were washed with culture medium, then fixed with 95% ethanol for 15 minutes at room temperature. The grafts were washed twice with distilled water, then treated with Gill's hemotoxylin (Fisher Scientific Co., Fairlawn, N.J.) for 2.5 minutes. The grafts were washed twice with distilled water, then exposed to Scott's tap water substitute (Fisher Scientific Co., Fairlawn, N.J.) for one minute. The grafts were washed twice with distilled water, twice with 95% ethanol, then mounted between a glass slide and cover slip for examination by light microscopy.

Application of Fluorescent Dyes

A 20 µg/ml solution of H33342 (Sigma Chemical Co., St. Louis, MO) in Dulbecco's Phosphate Buffered Saline (PBS), pH 7.4 was prepared fresh for each use. A 10 µg/ml solution of mithramycin (Sigma Chemical Co., St. Louis, MO) was prepared by combining 0.5 ml of mithramycin stock solution (0.2 mg/ml in PBS), 0.5 ml of a magnesium chloride solution (300 mM in PBS), and 9 ml of culture medium. Nile Red (Eastman Kodak Co., Rochester, New York) was first dissolved in acetone at i mg/ml and then diluted 1:100 in PBS to give a final concentration of 10 µg/ml. Sulfofluorescein diacetate (Molecular Probes, Junction City, OR) was used at a concentration of 20 µg/ml in PBS. A 4 mg/ml stock solution of rhodamine 123 (Molecular Probes, Junction City, OR) in DMSO was diluted 1:1000 in culture medium to give a final concentration of 4 μg/ml. All solutions were filtered through Gelman 0.2 micron disposable filters (Gelman Science, Inc., Ann Arbor, MI) for sterilization prior to use.

Endothelial cells were treated with dye in three ways. Seeded Beem capsules were washed once with culture medium, then immersed in dye solution for 30 to 90 minutes at 37° C. Alternatively, cells grown to confluence in culture flasks were treated with trypsin, pelleted by centrifugation for 6 minutes at 300×g, resuspended in dye solution, and incubated for 30 to 90 minutes at 37° C. These cells were then seeded onto graft material and incubated for varying lengths of time to permit cell adherence. Finally, in the case of rhodamine 123, H33342, and mithramycin, cells were cultured for up to five days at 37° C. in culture medium containing varying concentrations of these compounds, then seeded onto graft material. All endothelial cells, (labelled and control), were then visualized by fluorescence or light microscopy after seeding onto graft material.

Fluorescence Labeling of Endothelial Cells with PKHz6-GL

Microvessel endothelial cells were isolated from canine falciform ligament fat. Prior to treatment of a vascular graft with these cells the cells were labelled with the fluorescent dye PKH26-GL according to the protocol developed by Zynaxis Cell Science, Inc. Cells were incubated with this fluorescent dye for five minutes at room temperature and the reactions stopped by adding 2.5 ml of 25% serum albumin for one minute. The cells were subsequently washed with fetal bovine serum containing media 199 E by centrifugation. The fluorescently labelled cells were then resuspended in media 199 E containing autologous canine serum. The fluorescently labelled cells were then immediately sodded onto the lumenal surface of vascular grafts and implanted into canine carotid arteries. After three weeks of implantation animals were taken back to the operating room, anesthetized, and the vascular grafts removed. The grafts were cut in half lengthwise, fixed in 4% paraformaldehyde for one hour and subsequently washed with bovine serum albumin in phosphate buffered saline at a pH of 7.4. The lumenal surface of the grafts were evaluated from the proximal to distal anastomosis and representative photomicrographs obtained.

Florescence Microscopy

Fluorescence microscopy was performed using a Nikon diaphot microscope. Excitation and emission wavelengths were controlled by specific combinations of excitation and emission barrier filters in a dichroic filter combination (380 nm dichroic mirror for H33321 and sulfofluorescein diacetate; 510 nm dichroic mirror for mithramycin; 550 nm dichroic mirror for Nile Red and rhodamine 123).

Adherence Studies

The effects of various dyes on endothelial cell adherence to polystyrene was determined as follows. Cultured microvessel endothelial cells were incubated for 90 minutes at 37° C. in one of nine solutions. These were 20 μg/ml H33342 in Dulbecco's PBS; 10 μg/ml mithramycin in complete medium 199; 10 μg/ml Nile Red and 1% acetone in Dulbecco's PBS; 20 μg/ml SFDA in Dulbecco's PBS; and 4 μg/ml (10 μM) rhodamine 123 and 0.1% DMSO in complete medium 199. As controls, cells were also incubated in plain complete medium 199; plain Dulbecco's PBS; Dulbecco's PBS containing 1% acetone; and complete medium 199 containing 0.1% DMSO. The cells were washed twice by centrifugation for 6 minutes at 300×g, resuspended in plain complete medium 199 and seeded in triplicate in gelatin-coated 24 well plates at a density of $1.96 \times 10^4$ cells/cm$^2$. After 60 and 120 minutes, the medium was aspirated, 0.5 ml trypsin solution added to each well and the cells incubated for 10 minutes at 37° C. 0.2 ml of the resultant cell suspension was then added to a 9.8 ml Isoton and the number of adherent cells per well determined using a Coulter counter.

Growth Curve Determination

Cultured perirenal fat microvessel endothelial cells were incubated for 90 minutes in culture medium containing 10 μM rhodamine 123 and 0.1% DMSO, culture medium containing 0.1% DMSO alone, or plain culture medium. The cells were washed by centrifugation for 6 minutes at 300 x g and seeded in 24 well gelatinized polystyrene culture plates at an initial density of $0.5 \times 10^5$ cells per cm$^2$. The cells were grown in plain culture medium, or culture medium plus 0.1% DMSO 10 μM rhodamine 123. At designated time points the medium was aspirated, the cells washed once with medium and treated with 0.5 ml trypsin for 10 minutes at 37° C. 0.2 ml of this suspension was added to 9.8 ml of Isoton solution and the cells counted in a Coulter counter.

Statistics

EC cell number in each study was determined by counting cells with a Coulter counter for three replicate experiments and expressed as cell number ± standard error of the mean. For adherence studies, experimental values were compared to control samples using the Student's T-test. Growth curve analysis was performed using linear regression analysis. Statistical significance was chosen at p less than 0.05.

Results

1. Staining Properties

Experiments involving H33342 (20 μg/ml) and mithramycin (10 μg/ml) demonstrated that incubating human aorta, iliac vein and microvessel endothelial cells for 90 minutes at 37° C. resulted in successful labeling of the cell nucleus. Similarly, Nile Red, rhodamine 123 and SFDA at a concentration of 20 μg/ml were effective at fluorescently labeling the cell cytoplasm.

A serious disadvantage of H33342, mithramycin, Nile Red, and SFDA was that the wavelengths required to visualize these dyes were associated with significant autofluroescence of the polyethyleneterephthalate polyester and ePTFE graft material. While endothelial cells treated with these four dyes could be visualized on the grafts, it was often difficult to distinguish cells from the background. A second difficulty encountered with these dyes was the high degree of non-specific incorporation of the dyes into the graft material. In the absence of cells, graft material treated with any of these four dyes for 90 minutes at 37° C. showed discrete areas of fluorescence that could be mistaken for cells. For these reasons, H33342, mithramycin, sulfofluorescein diacetate, and Nile Red were unacceptable for our purposes.

To examine the effects of rhodamine 123, human microvessel endothelial cells were incubated for 90 minutes at 37° C. in culture medium containing 1, 5, 10, 20 and 100 μM rhodamine 123 (0.4, 2.0, 4.0, 8.0, 40.0 μg/ml) and the appropriate dilution of DMSO and examined by fluorescent microscopy. There was a concentration-dependent increase in intensity of fluorescence. Cells treated with 1 μM rhodamine 123 demonstrated faint fluorescence while incubation in 100 μM solution produced strong fluorescence.

When cells were labelled with rhodamine 123 (4 μg/ml) followed by incubation on either DACRON polyester, ePTFE or PVA surfaces, excellent cytoplasmic visualization was obtained with minimal surface autofluorescence. Excitation and emission wavelength were 510 nm and 590 nm, respectively, in all cases.

Cells which have been stained with the fluorescent dye PKH26-GL show a homogenous incorporation of this dye into all of the membranous components. Cells labelled with this dye and in grown in tissue culture show a homogenous distribution of stain in the paranuclear area presumably due to the high concentration of membrane bound organelles in this area of cells. This dye showed excellent retention of intensity during examination under a fluorescence microscope. Endothelial cells treated with this dye and subsequently cultured exhibited no change in general morphology when observed by phase contrast microscopy.

2. Adherence Effects

The adherence of microvessel endothelial cells to polystyrene was examined for each of the five fluorescent dyes. Cells were preincubated with each dye at concentrations listed in the methods for 90 minutes. Following labelling, the cells were seeded onto polystyrene at $1.96 \times 10^4$ cells/cm$^2$ and incubated for 1 and 2 hours. At that time, the surface was vigorously washed twice. The cells remaining on the surface were counted following brief trypsinization. The number of remaining cells is shown in FIG. 1. When compared to unlabelled control cells, H33342 Nile Red and SFDA demonstrated a significant effect on subsequent cell adherence a measured at 60 and 120 minutes. Mithramycin and rhodamine 123 had no effect on cellular adherence.

3. Growth Effects After Labelling With Rhodamin 123

Figure 2:
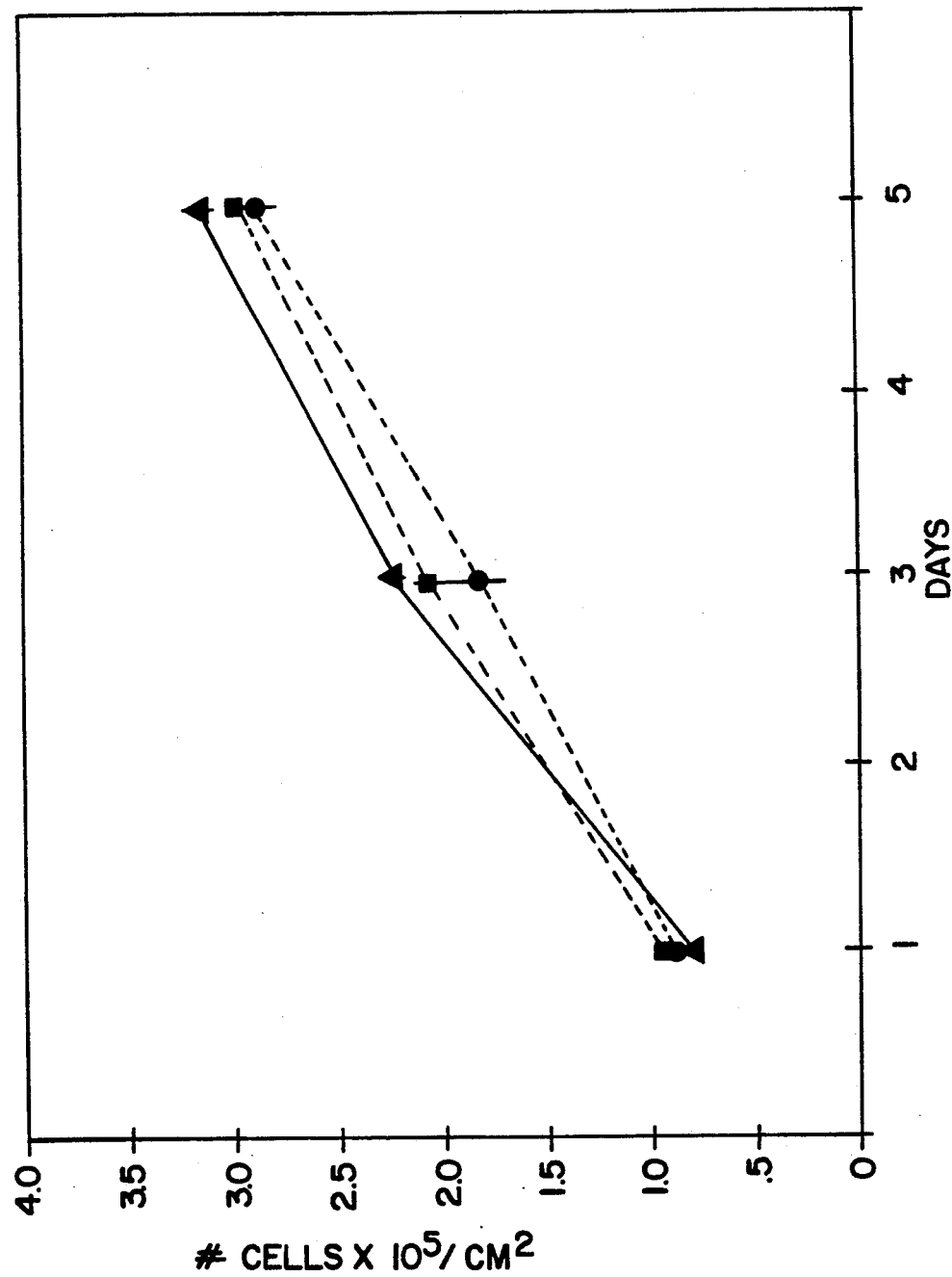
FIG. 2: Growth curves demonstrating the effect of pre-treatment with 10 $\mu$M rhodamine 123 on human microvessel endothelial cells. Cells were incubated for 90 minutes in one of three media: 1. Culture medium (▲); 2. Culture medium containing 0.1% DMSO (●); or 3. Culture medium containing (■) 0.1% DMSO and 10 $\mu$M rhodamine 123 (■). Following incubation, the cells were washed and seeded onto gelatin coated polystyrene at $5 \times 10^4$ cells/cm$^2$ and maintained in culture medium. Cell number was determined on days 1, 3, and 5 and expressed as the mean ± standard error of the mean. Multiple regression analysis revealed no statistical difference in cell number. This suggests that pre-labelling with rhodamine 123 has a minimal effect on cell growth.

Since rhodamine 123 allowed optimal visualization of endothelial cells on graft surfaces, the effect of labelling the cells prior to growth in culture was examined. Endothelial cells were preincubated with culture medium, medium containing 0.1% DMSO or medium containing 0.1% DMSO and 10 μM rhodamine 123. Following preincubation and washing, the cells were seeded at an initial concentration of $0.5 \times 10^5$ cells per cm$^2$ and placed in culture. Cell number was determined on days 1, 3 and 5. The growth curves in FIG. 2 show little difference in subsequent cell growth in culture medium 199 between prelabelled and unlabelled cells.

4. Growth Curves In Medium Containing Rhodamine 123

Figure 3:
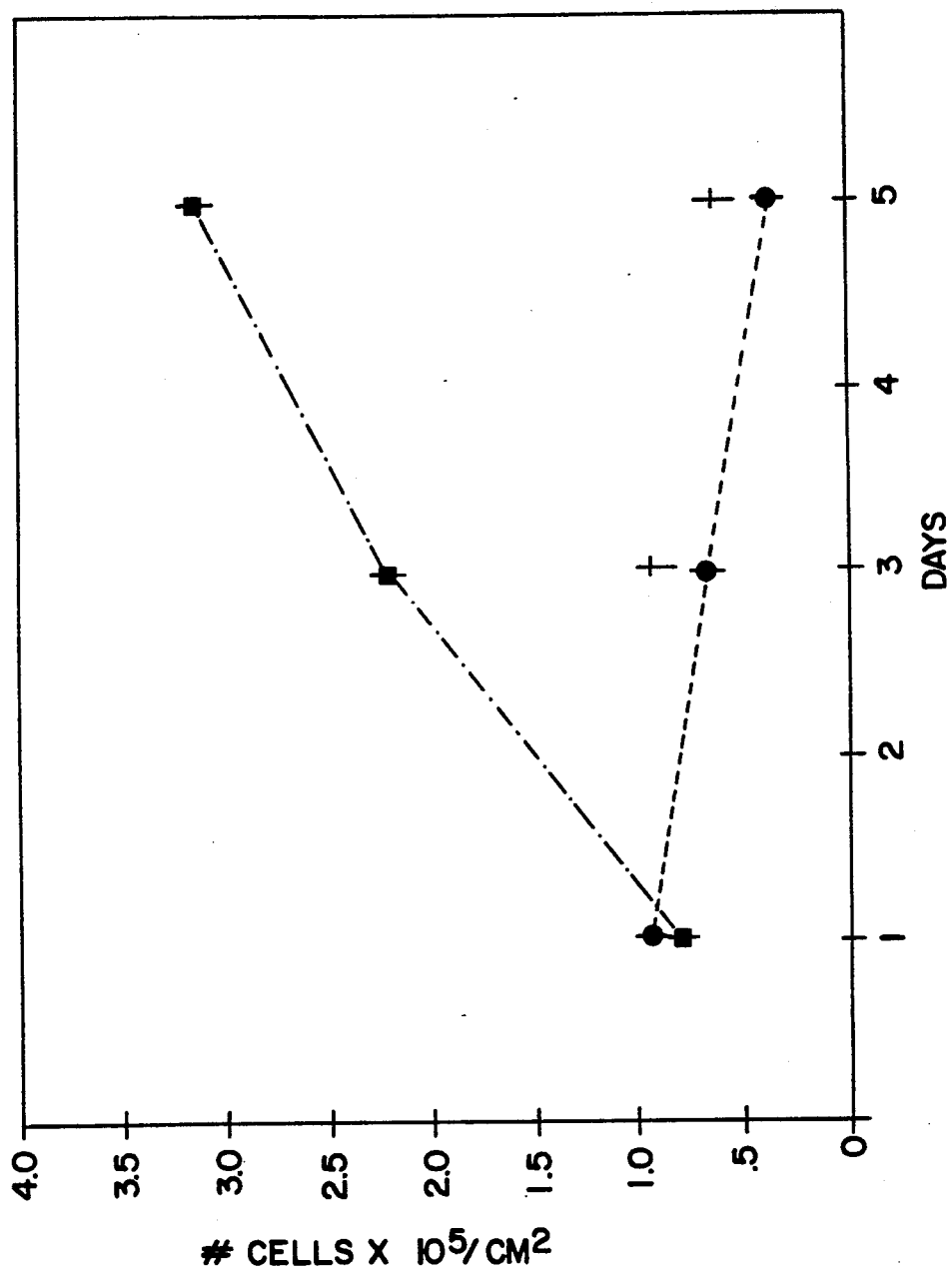
FIG. 3: Growth curves demonstrating the effect of culture medium containing rhodamine 123 on human microvessel endothelial cells. Cells were washed and seeded onto gelatin coated polystyrene at $5 \times 10^4$ cells/cm$^2$ and maintained in culture medium containing 10 $\mu$M rhodamine 123 (●) or culture medium containing no rhodamine 123 (■). Cell number was determined on days 1, 3 and 5 and expressed as the mean ± standard error of the mean. Multiple regression analysis revealed a statistical difference in cell growth between cells grown in rhodamine 123-containing medium versus culture medium. Prolonged contact with rhodamine 123 prevents cell growth in culture.

Since prelabelling of cells with rhodamine 123 had little effect on subsequent cell growth, the effect of continued rhodamine 123 in the culture medium was examined. Cells were seeded at $0.5 \times 10^5$ cells/cm$^2$ onto polystyrene and placed in culture. Culture medium for this growth curve study contained rhodamine 123 throughout the time of the study. Rhodamine 123 maintained in the culture medium prevented cell growth in culture (See FIG. 3).

5. Growth Effects After Labelling With PKH26-GL

Figure 4:
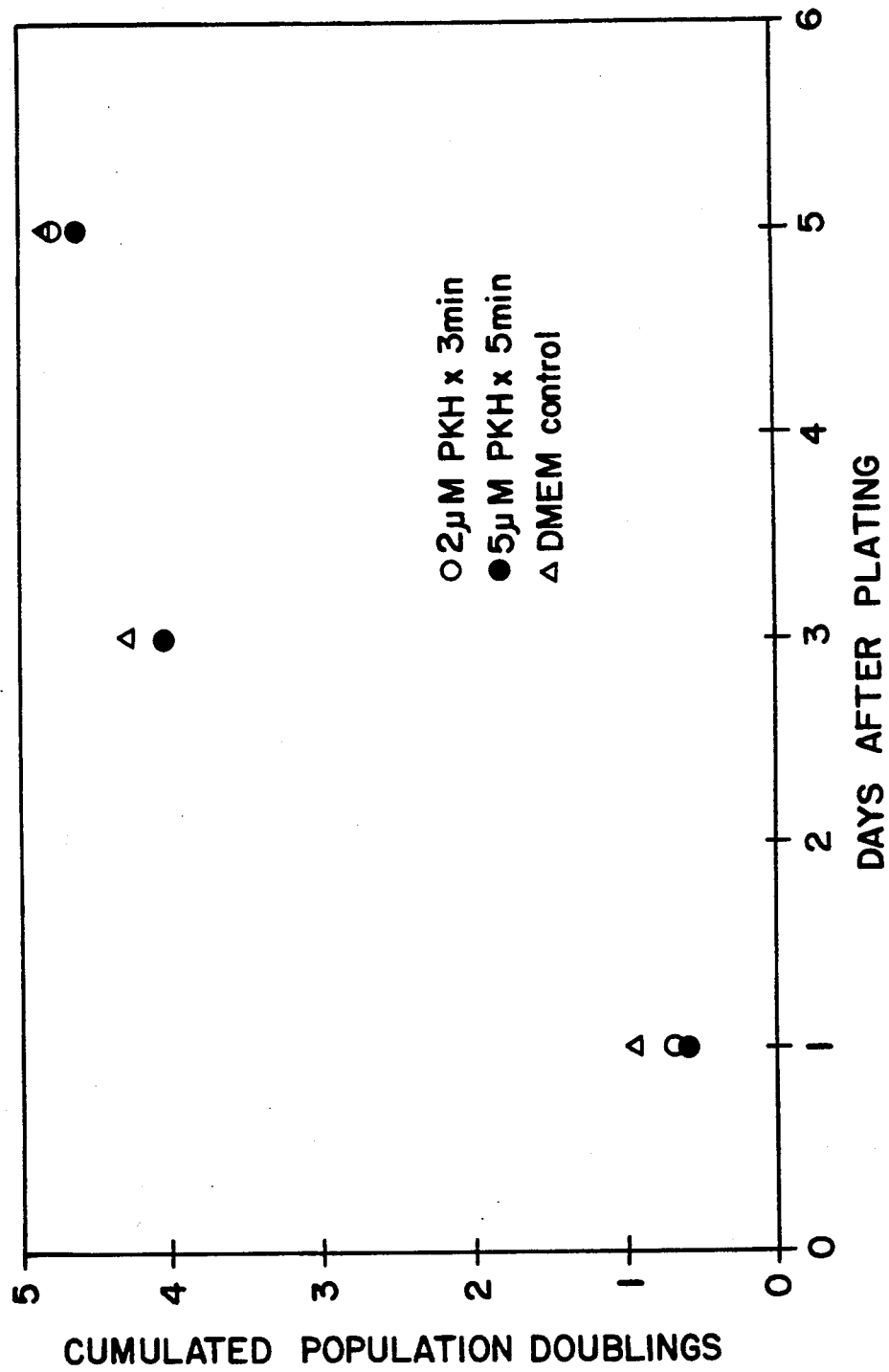
FIG. 4: A growth curve demonstrating that canine microvascular endothelial cells labelled with a fluorescent dye known as PKH26-GL grow at the same rate as identical cells which have not been treated with this fluorescent dye.
Figure 5:
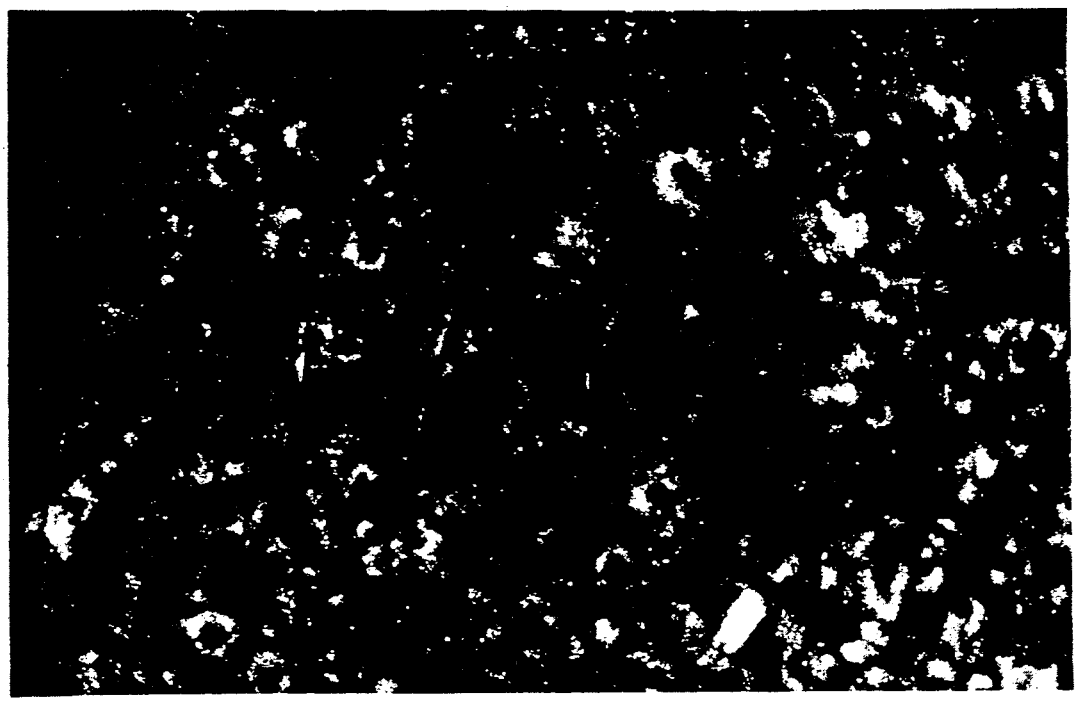
FIG. 5: A fluorescent micrograph representing microvascular endothelial cells which have been treated with a fluorescent dye know as PKH26-GL showing the distribution of fluorescence within the individual cells. The dark areas within each Cell are the nucleus of the cell does not take up the fluorescent dye.

Canine microvascular endothelial cells labelled with the fluorescent dye PKH26-GL grew at the same rate as identical cells not treated with this dye (See FIG. 4). FIG. 5, a fluorescent micrograph representing microvascular endothelial cells treated with PKH26-GL, shows the distribution of fluorescence within the individual cells. The dark areas within each cell are the nucleus of the cell which does not take up the fluorescent dye. The cells remained viable and labelled following three weeks of implantation in a dog (FIG. 6).

What is claimed is:

1. A method of determining uncultured microvascular endothelial cell coverage and cell-to-cell interactions on a prosthetic surface, which is performed prior to implantation of a prosthesis, comprising
   (a) providing a prosthetic surface which is at least translucent to light in a selected wavelength range;
   (b) applying uncultured microvascular endothelial cells to at least 50% confluence to said surface;
   (c) staining said uncultured microvascular endothelial cells with a selected non-toxic fluorescent dye capable of exhibiting fluorescent emission in said selected wavelength range; and
   (d) illuminating said uncultured microvascular endothelial cells with a light to excite said emission to permit observation of the cell coverage of said prosthetic surface, and
   (e) observing said prosthetic surface to determine that a monolayer of said uncultured microvascular endothelial cells has formed before said prosthesis is implanted.

2. The method of claim 1 wherein said surface does not autofluoresce in said selected wavelength range.

3. The method of claim 1 in which said surface is expanded polytetrafluoroethylene.

4. The method of claim 3 wherein said selected wavelength range is 500-600 nm.

5. The method of claim 1 wherein said surface is polyethyleneterephthalate.

6. The method of claim 5 wherein said selected wavelength range is 500-600 nm.

7. The method of claim 1 wherein said surface is transparent in said selected wavelength range.

8. The method of claim 1 wherein said surface is a vascular graft and wherein said applying step is performed on the interior surface of said graft.

9. The method of claim 1 wherein said dye is cytoplasmic.

10. The method of claim 9 wherein said selected wavelength range is 500-600 nm.

11. The method of claim 9 wherein said dye does not interfere with growth of said uncultured microvascular endothelial cells.

12. The method of claim 1 wherein said dye is rhodamine 123.

13. The method of claim 12 wherein said wavelength range is 500-600 nm and wherein said surface is expanded polytetrafluoroethylene, polyethyleneterephthalate or polyvinyl alcohol.

14. The method of claim 1 wherein said wavelength range is 500-600 nm and wherein said surface is expanded polytetrafluoroethylene, polyethyleneterephthalate or polyvinyl alcohol.

* * * * *